US008859216B2

(12) United States Patent
Yoon et al.

(10) Patent No.: US 8,859,216 B2
(45) Date of Patent: Oct. 14, 2014

(54) METHOD FOR NONINVASIVE PREDICTION OR DIAGNOSIS OF INFLAMMATION AND INFECTION IN AMNIOTIC FLUID OF PATIENTS WITH PREMATURE RUPTURE OF MEMBRANES

(75) Inventors: Bo Hyun Yoon, Seoul (KR); Joong Shin Park, Seoul (KR); Jong Kwan Jun, Seoul (KR); Chan Wook Park, Seoul (KR)

(73) Assignees: Snu R&DB Foundation, Seoul (KR); Ob Med, Seoul (KR)

( * ) Notice: Subject to any disclaimer, the term of this patent is extended or adjusted under 35 U.S.C. 154(b) by 0 days.

(21) Appl. No.: 14/343,147

(22) PCT Filed: Sep. 5, 2012

(86) PCT No.: PCT/KR2012/007111
§ 371 (c)(1),
(2), (4) Date: Mar. 6, 2014

(87) PCT Pub. No.: WO2013/036030
PCT Pub. Date: Mar. 14, 2013

(65) Prior Publication Data
US 2014/0212899 A1      Jul. 31, 2014

(30) Foreign Application Priority Data
Sep. 8, 2011  (KR) .......................... 10-2011-0091198

(51) Int. Cl.
*G01N 33/53* (2006.01)
*G01N 31/00* (2006.01)
*G01N 33/543* (2006.01)

(52) U.S. Cl.
CPC ................................ *G01N 33/54306* (2013.01)
USPC ........... 435/7.21; 435/7.1; 436/501; 436/518; 424/9.1; 424/520; 422/430; 530/300; 530/350

(58) Field of Classification Search
None
See application file for complete search history.

(56) References Cited

FOREIGN PATENT DOCUMENTS

| JP | 2010-002180 A | 1/2010 |
| KR | 10-1997-0000247 A | 1/1997 |

OTHER PUBLICATIONS

The International Search Report for International Application No. PCT/KR2012/007111, four pages, mailed Feb. 28, 2013.
Yoon, Bo-Hyun et al., "Establishment of pathophysiology and prevention of fetal diseases", Seoul National University, Research Report, (2002).
Yoon, Bo-Hyun et al., "Establishment of pathophysiology and prevention of fetal diseases", Seoul National University, Research Report, (2004).

*Primary Examiner* — Lisa Cook
(74) *Attorney, Agent, or Firm* — Vorys, Sater, Seymour and Pease LLP; Mihsun Koh

(57) ABSTRACT

Provided is a method for noninvasive prediction or diagnosis of inflammation and/or infection in amniotic fluid leaked through the cervix into the vagina to predict the concentration of inflammatory markers in the amniotic fluid inside uterus by measuring the concentration of inflammatory markers (various cytokines). Further provided is a method for prediction or diagnosis of inflammation and/or infection in amniotic fluid by measuring the concentration of markers (IL-6, IL-1β IL-8, MCP-1, GRO-α) in the amniotic fluid leaked through the cervix into the vagina in patients with premature rupture of membranes. The method can be performed more stably on pregnant women, as compared to the conventional method for prediction or diagnosis of inflammation and/or infection using invasively collected amniotic fluid.

11 Claims, 10 Drawing Sheets

JJun JK, Yoon BH *et al., Am J Obstet Gynecol* 2000; 183:868-873

METHOD FOR NONINVASIVE PREDICTION OR DIAGNOSIS OF INFLAMMATION AND INFECTION IN AMNIOTIC FLUID OF PATIENTS WITH PREMATURE RUPTURE OF MEMBRANES

TECHNICAL FIELD

The present invention relates to a method for noninvasive prediction or diagnosis of inflammation and infection in amniotic fluid.

BACKGROUND ART

Inflammation and/or infection in amniotic fluid is a risk factor for preterm birth and adverse neonatal outcome, which is present in about 50% of patients with preterm premature rupture of membranes. The prediction or diagnosis of infection/inflammation in amniotic fluid can be performed by microbial culture and amniotic fluid analysis, such as measuring inflammatory markers (cytokine concentration, matrix metal loproteinase enzyme concentration, white blood cell count, etc.). The amniotic fluid analysis method is the most sensitive and specific method for predicting the possibility of preterm birth and assessing the risk for neonatal complications. However, collecting amniotic fluid for analysis requires abdominal amniocentesis, which is an invasive procedure. In particular, as it is often difficult to perform amniocentesis when the volume of amniotic fluid is reduced in patients with premature rupture of membranes, therefore only ⅔ of patients undergo this procedure in US.

Although it is preferable to use amniotic fluid for assessing the inflammation in amniotic fluid, an alternative method using vaginal secretion for predicting inflammation or infection is suggested, because it is an invasive procedure. However, as there is a higher chance of infection since the vaginal fluid is exposed to outside, it is difficult to use vaginal fluid for prediction of inflammation or infection in amniotic fluid. It has also been confirmed that there is a significant difference in the absolute amount of inflammatory markers when compared with amniotic fluid. It has been confirmed that vaginal fluid can not have the predictability as much as the invasively collected amniotic fluid can.

In previous research, the present inventors proved a strong correlation between the concentrations of interleukin-6 (IL-6) in cervical secretion collected by Dacron polyester swab and those in the amniotic fluid collected by abdominal amniocentesis from patients diagnosed with premature rupture of membranes (Jun J K, Yoon B H et al., Am J Obstet Gynecol 183:868-873, 2000). However, as there is a significant difference between the absolute concentrations of two subject samples, it is difficult to apply the cut-off value of IL-6 in the amniotic fluid collected by abdominal amniocentesis to cervical secretion for analysis of inflammation or infection in amniotic fluid (see FIG. 1). Similar results were reported from other investigators demonstrating that the concentration of IL-6 in the amniotic fluid (see FIG. 2a) was lower than that of the IL-6 concentration in cervical secretion (see FIG. 2b) (Rizzo G et al., Gynecol Obstet Invest 1998; 46: 91-5)(see FIG. 2). In addition, the previous research showed that the median value or average value of inflammatory cytokine in cervical secretion was generally measured in pg/ml units, while the median value or average value of cytokine in amniotic fluid was measured in ng/ml units. As the concentration of inflammatory cytokine in cervical secretion is extremely lower than those in amniotic fluid, it is difficult to directly use the concentration of cytokine in cervical fluid to predict the concentration of cytokine in amniotic fluid.

Also, in the previous study of the present inventors on counting white blood cell for measuring the level of inflammation in amniotic fluid, the present inventors confirmed a significantly higher number of white blood cells in amniotic fluid leaked through the cervix than that of white blood cells in amniotic fluid collected by abdominal amniocentesis, suggesting that white blood cell count in amniotic fluid leaked through the cervix was not suitable to be used as a marker for predicting inflammation or infection (see FIG. 3 and Table 1). Matrix metal loproteinase-8 (MMP-8) is known to be the best marker for predicting the level of inflammation and the development of preterm birth and neonatal complications. However, it is difficult to use MMP-8 in fluid leaked through the cervix as a prediction marker for inflammation or infection in amniotic fluid, since in most cases, there was a significant increase in the concentration in amniotic fluid leaked through the cervix, even though the concentration in amniotic fluid collected by abdominal amniocentesis was low (See FIG. 10 and Table 8). On the contrary, IL-10 which is used for determining the level of inflammation in amniotic level was not suitable to be used as a marker for predicting inflammation or infection in amniotic fluid, because IL-10 concentration in amniotic fluid leaked through the cervix decreased significantly, even though the concentration was high in amniotic fluid collected by abdominal amniocentesis (See FIG. 9 and Table 7).

Accordingly, the level of inflammatory markers in vaginal secretion was measured to determine the inflammation or infection in amniotic fluid noninvasively. However, finding a noninvasive method for prediction of inflammation or infection in amniotic fluid was not easy, since there were significant differences in absolute values between inflammatory markers in vaginal secretion and those in amniotic fluid. Therefore, it is important to prove the correlation between inflammatory markers in amniotic fluid collected from patients with premature rupture of membranes by abdominal amniocentesis and those in the amniotic fluid leaked through the cervix into the vagina, and furthermore to prove similarities in their absolute concentrations. These will provide a significant improvement in prediction or diagnosis of infection and/or inflammation in amniotic fluid by analyzing the amniotic fluid leaked through the cervix without performing invasive abdominal amniocentesis in patients with premature rupture of membranes.

TABLE 1

Sensitivity and specificity for predicting infect ion/inflammation in amniotic fluid according to each of the cut-off values of white cell count in the amniotic fluid leaked through the cervix into the vagina.

| Cutt-off value (cells/mm$^2$) | Sensitivity | Specificity |
| --- | --- | --- |
| 100 | 90.9% (10/11) | 26.7% (6/15) |
| 500 | 72.7% (8/11) | 53.3% (8/15) |
| 1000 | 54.5% (6/11) | 66.7% (10/15) |

Until now, there has been no investigation on noninvasive prediction of infection/inflammation in the uterus by comparing the absolute values and by determining correlation of various markers between amniotic fluid collected from patients with premature rupture of membranes by abdominal amniocentesis and amniotic fluid leaked through the cervix into the vagina. Instead of using special equipment to collect amniotic fluid from posterior fornix, most of the previous studies used basic equipment such as bags or vacuum bulb.

This caused the increased risk of contamination by bacteria in the vagina, making amniotic fluid from posterior fornix difficult to be used in prediction of infection/inflammation in the uterus. Therefore, in most studies, the amniotic fluid leaked through the cervix into the vagina was used for only determining the fetal pulmonary maturity. Most of the recent studies have focused on confirming the usefulness of phosphatidylglycerol (PG) in predicting the fetal pulmonary maturity from amniotic fluid collected from patients with premature rupture of membranes (Stedman C M et al., Am J Obstet Gynecol 140:34-38, 1981).

The present inventors have measured the concentration of cytokines including IL-6 (Interleukin-6), IL-1 (Interleukin-1), IL-8 (Interleukin-8), monocyte chemo-attractant protein-1 (MCP-1) and Growth Related Oncogene-α (GRO-α) as inflammatory markers. As a result, the present inventors indentified a correlation in the amount of inflammatory markers between the amniotic fluid collected from patients with premature rupture of membranes by abdominal amniocentesis and noninvasively collected amniotic fluid leaked through the cervix into the vagina. The usefulness of 5 cytokines to predict inflammation or infection in amniotic fluid was also confirmed on the basis of the similarity in order of concentration. The present inventors confirmed that these cytokines in amniotic fluid leaked through the cervix into the vagina can be effectively used as inflammatory markers for predicting or diagnosis of inflammation/infect ion in amniotic fluid, thereby leading to the completion of the present invention.

DISCLOSURE

Technical Problem

One objective of the present invention is to provide a method for noninvasive prediction or diagnosis of inflammation and/or infection in amniotic fluid by predicting the concentration of inflammatory markers in the amniotic fluid inside uterus through measuring the concentrations of inflammatory markers (various cytokines) in amniotic fluid leaked through the cervix into the vagina.

Another objective of the present invention is to provide a kit for prediction or diagnosis of inflammation and infection in amniotic fluid using amniotic fluid leaked through the cervix into the vagina, which includes an antibody binding specifically to above-mentioned inflammatory markers.

Still another objective of the present invention is to provide a biochip for prediction or diagnosis of inflammation and/or infection in amniotic fluid, in which biomolecules binding specifically to above-mentioned inflammatory markers are integrated to a solid substrate.

Technical Solution

In order to achieve the objectives, the present invention provides a method for measuring the concentration of inflammatory markers in amniotic fluid leaked through the cervix into the vagina for prediction or diagnosis of inflammation or infection in amniotic fluid. The method includes the steps of:

1) measuring the concentration of an inflammatory marker in amniotic fluid leaked through the cervix into the vagina collected from patients with premature rupture of membranes; and 2) assessing the risk for inflammation or infection when the concentration of the inflammatory marker of Step 1 is higher than the cut-off value.

The present invention also provides a kit for prediction or diagnosis of inflammation and infection in amniotic fluid using amniotic fluid leaked through the cervix into the vagina, which includes an antibody binding specifically to above-mentioned inflammatory markers.

Furthermore, the present invention provides a biochip for prediction or diagnosis of inflammation and infection in amniotic fluid, in which biomolecules binding specifically to above-mentioned inflammatory markers are integrated to a solid substrate.

Advantageous Effects

Compared to the conventional method for prediction or diagnosis of inflammation and infection in amniotic fluid by using invasively collected amniotic fluids, the method of the present invention can be performed more stably on pregnant women by using noninvasively collected amniotic fluid that is leaked through the cervix.

(a) concentration of IL-6 in the amniotic fluid induced according to the presence or absence of positive cultures in the amniotic fluid;

(b) concentration of IL-6 in cervical discharge induced according to the presence or absence of positive cultures in the amniotic fluid; and (c) ROC curve of IL-6 in amniotic fluid (● and full line) and in cervical secretion (○ and dashed line) for the prediction of positive amniotic fluid culture.

Figure 1:
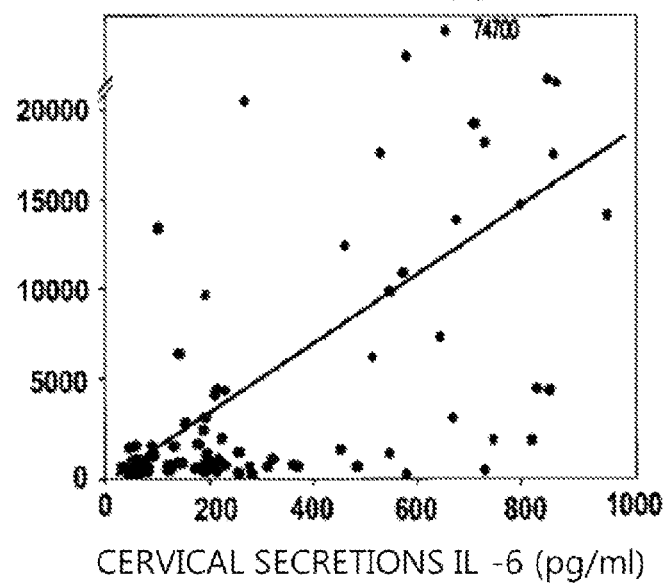
FIG. 1 is a graph confirming that there was the correlation between the concentration of interleukin-6 (IL-6) in cervical secretion acquired by Dacron polyester Swab and that in amniotic fluid acquired by transabdominal amniocentesis, but that there was a big difference in the absolute concentration and threshold value.
Figure 2:
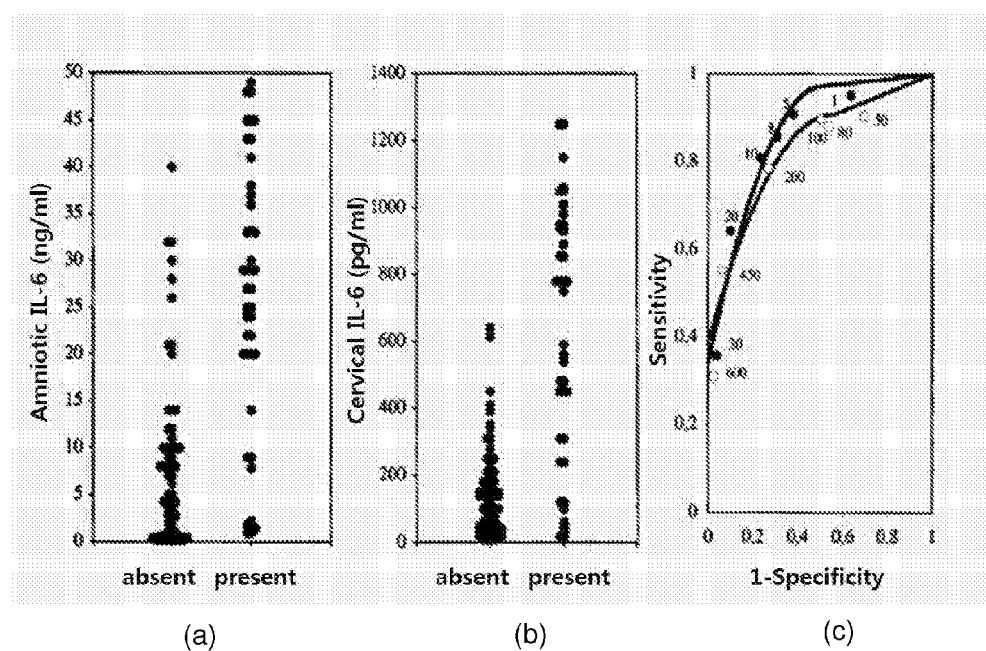
FIG. 2 is a graph showing the concentration of IL-6 in amniotic fluid (a) or in cervical discharge (b) depending on the presence or absence of infection in the amniotic fluid collected by transabdominal amniocentesis, and Receiver Operating Characteristic (ROC) curve (c)
Figure 3:
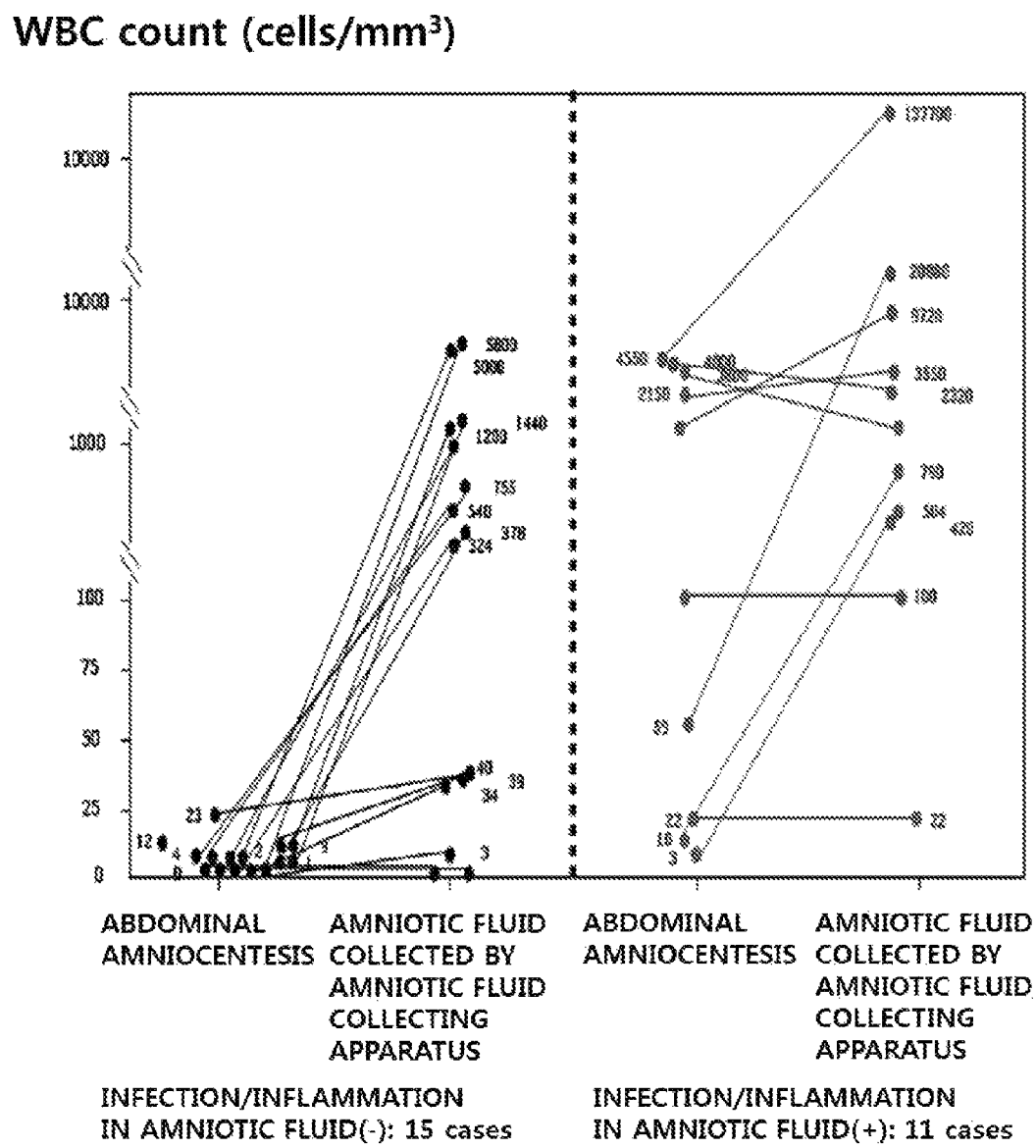

FIG. 3 is a graph comparing white blood cell count in the amniotic fluid collected by transabdominal amniocentesis with that in the amniotic fluid leaked from the cervix into vagina in pregnant women diagnosed with premature rupture of membranes.

Figure 4:
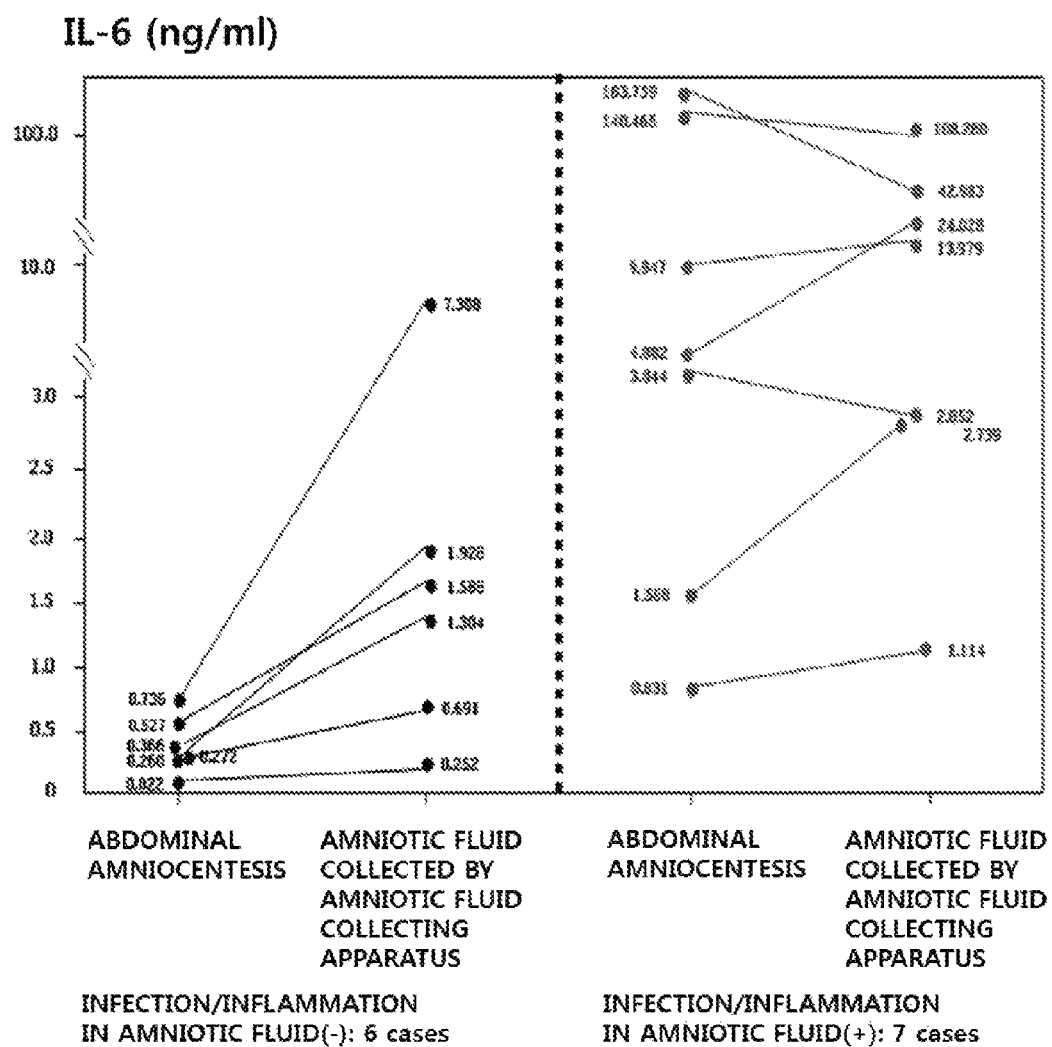

FIG. 4 is a graph comparing the concentration of IL-6 in the amniotic fluid collected by transabdominal amniocentesis with that in amniotic fluid leaked from the cervix into vagina in pregnant women with premature rupture of membranes.

Figure 5:
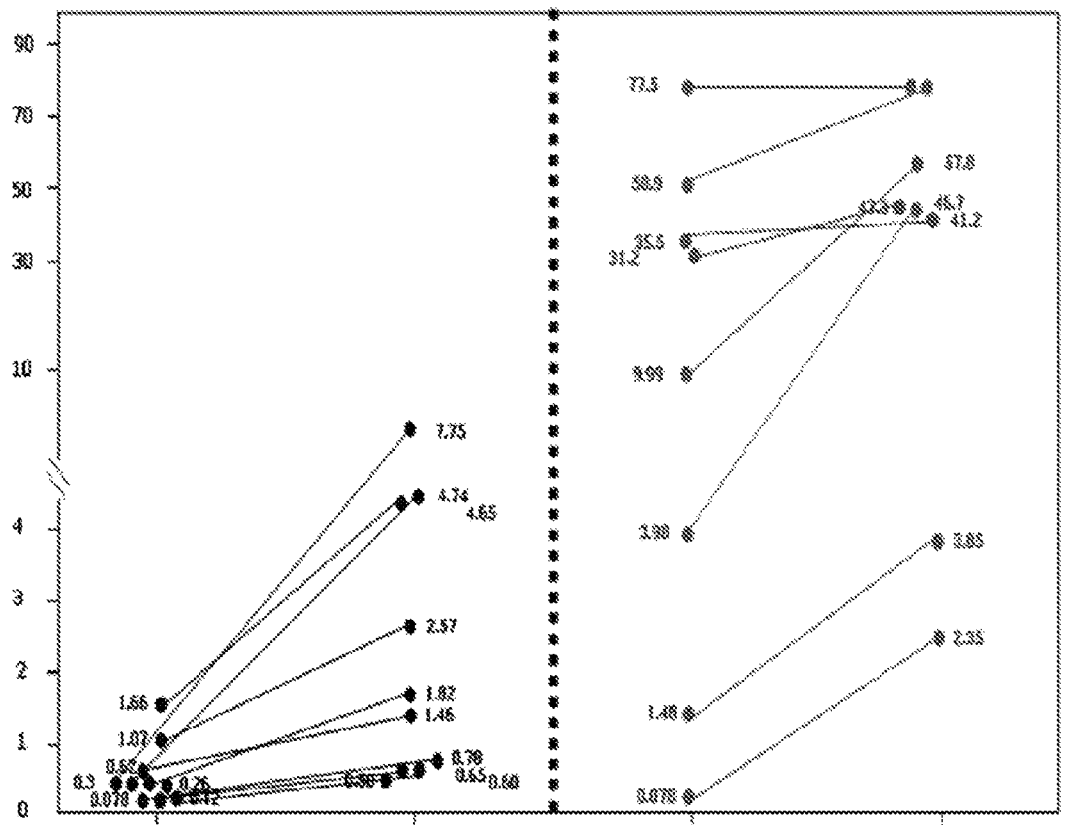

FIG. 5 is a graph comparing the concentration of IL-8 in the amniotic fluid collected by transabdominal amniocentesis with that in amniotic fluid leaked from the cervix to vagina in pregnant women with premature rupture of the membrane.

Figure 6:
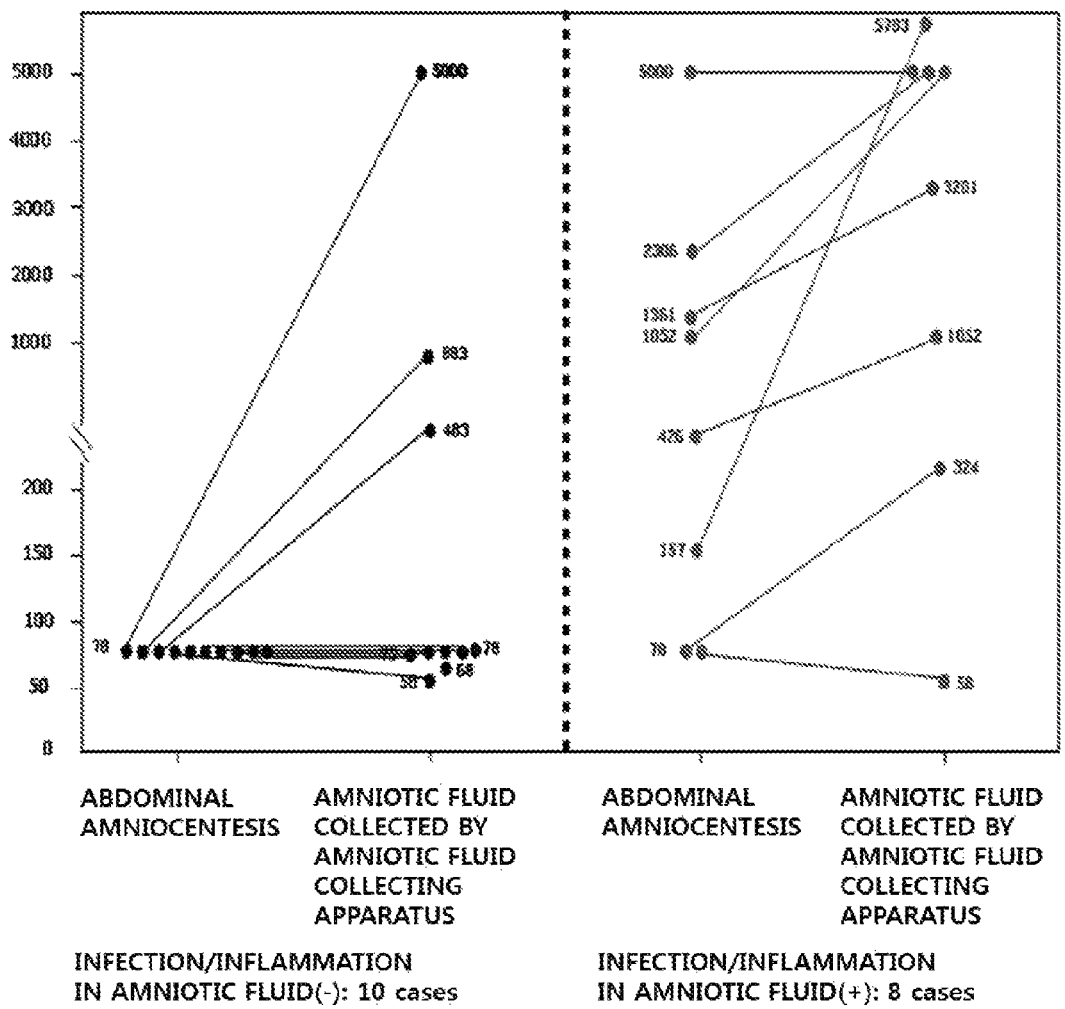

FIG. 6 is a graph comparing the concentration of IL-1β in the amniotic fluid collected by transabdominal amniocentesis with that in amniotic fluid leaked from the cervix into vagina in pregnant women with premature rupture of membranes.

Figure 7:
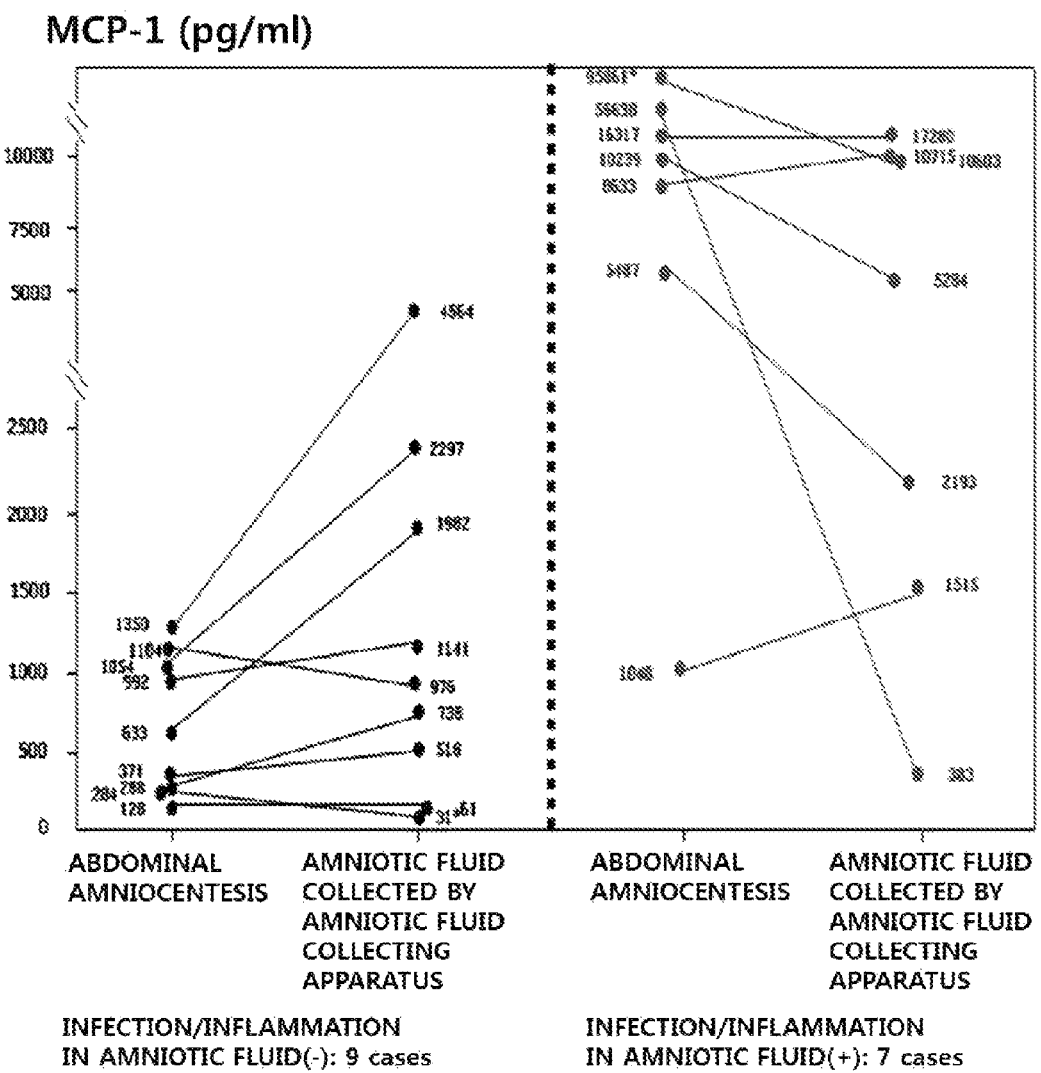

FIG. 7 is a graph comparing the concentration of monocyte chemoattractant protein-1 (MCP-1) in the amniotic fluid collected by transabdominal amniocentesis with that in amniotic fluid leaked from the cervix into vagina in pregnant women with premature rupture of membranes.

Figure 8:
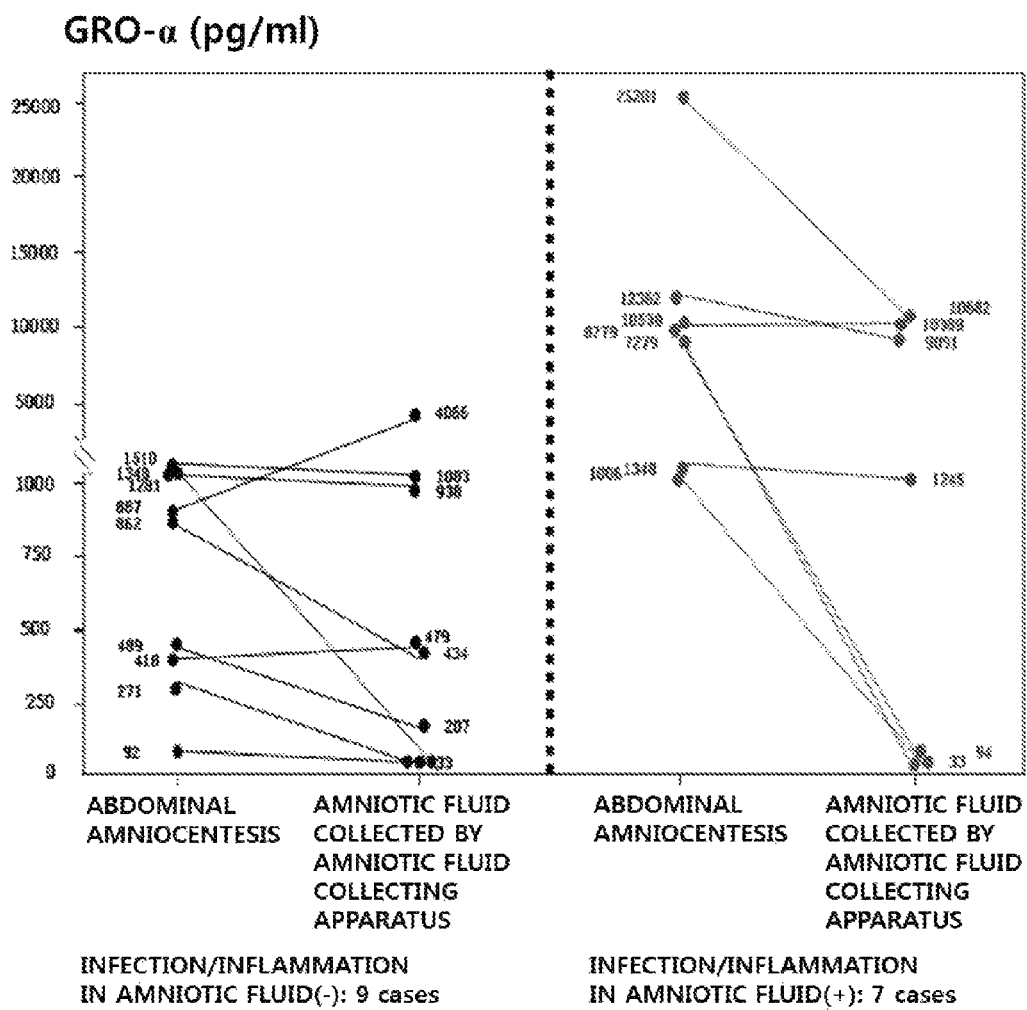

FIG. 8 is a graph comparing the concentration of GRO-α (Growth Related Oncogene-α) in the amniotic fluid collected by transabdominal amniocentesis with that in the amniotic fluid leaked from the cervix into vagina in pregnant women with premature rupture of membranes.

Figure 9:
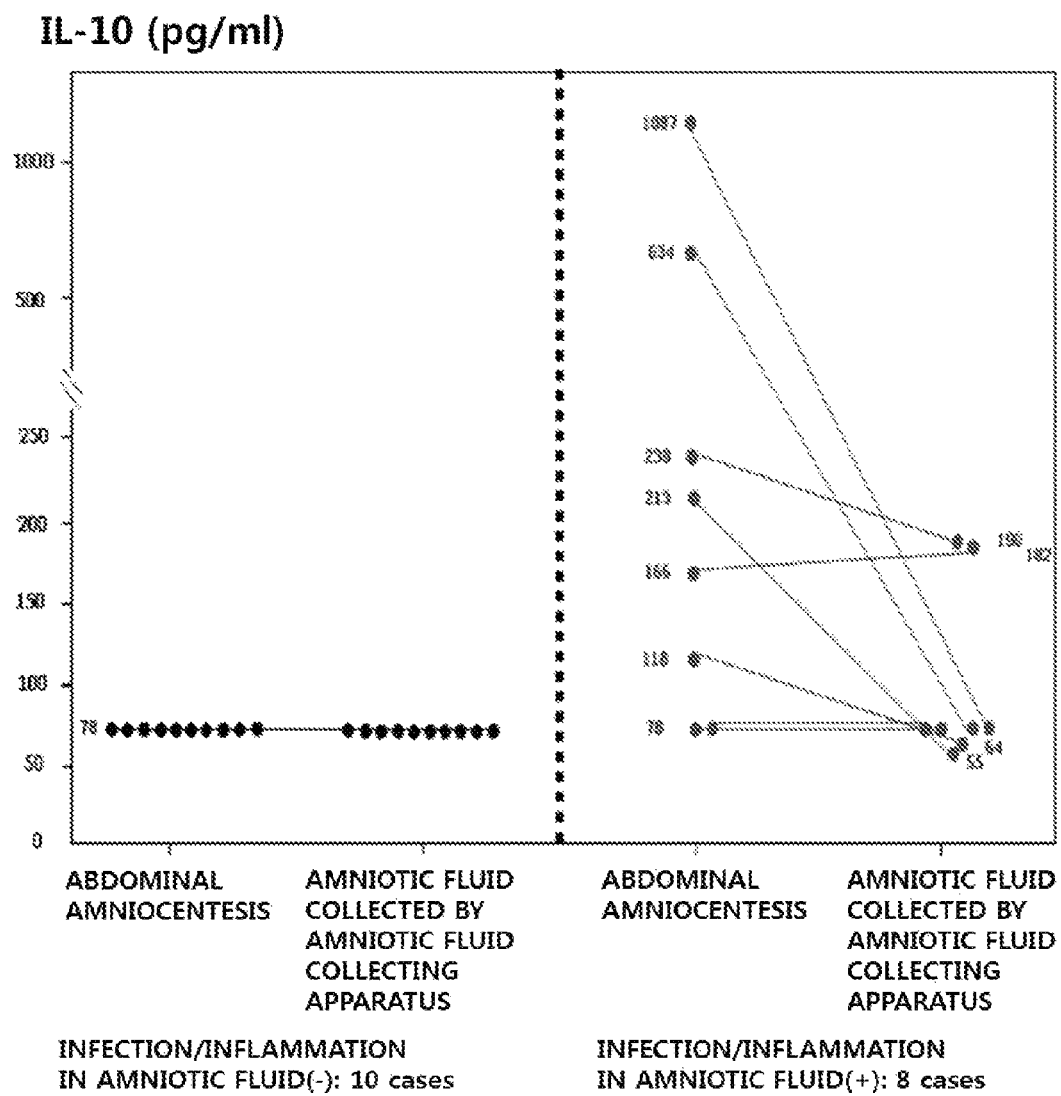

FIG. 9 is a graph comparing the concentration of IL-10 in the amniotic fluid collected by transabdominal amniocentesis with that in the amniotic fluid leaked from the cervix into vagina in pregnant women with premature rupture of membranes.

Figure 10:
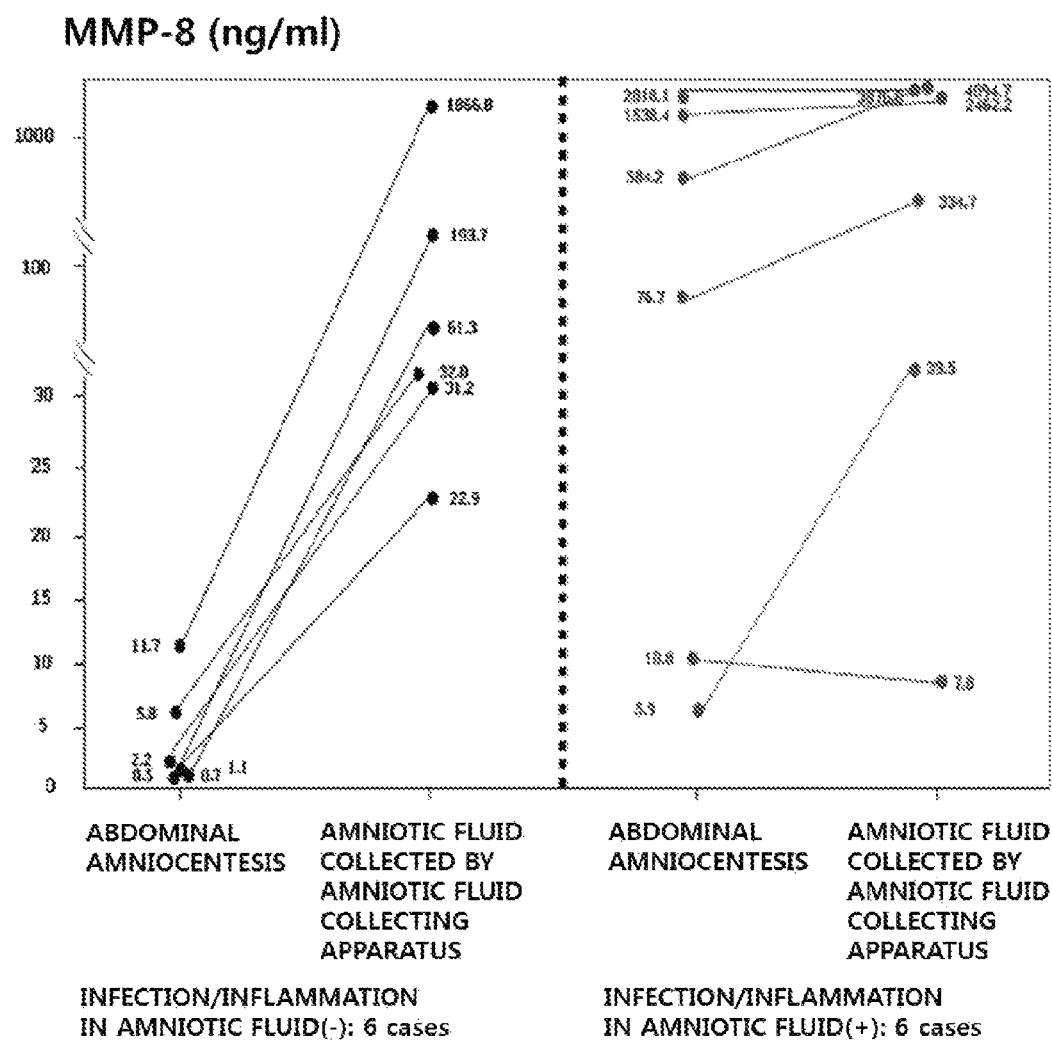

FIG. 10 is a graph comparing the concentration of matrix metal 1 loproeinase-8 (MMP-8) in the amniotic fluid collected by transabdominal amniocentesis with that in amniotic fluid leaked from the cervix into vagina in pregnant women with premature rupture of membranes.

BEST MODE

Hereinafter, the present invention will be described in detail.

The present invention provides a method for measuring the concentration of inflammatory markers in amniotic fluid leaked through the cervix into the vagina for prediction or diagnosis of inflammation and/or infection in amniotic fluid. The method includes the steps of:

1) measuring the concentration of an inflammatory marker in amniotic fluid leaked through the cervix into the vagina collected from patients with premature rupture of membranes; and 2) assessing the risk for inflammation or infection when the concentration of the inflammatory marker of Step 1 is higher than the cut-off value.

The marker is an inflammatory marker, preferably cytokine, and more preferably one selected from the group consisting of interleukin-6 (IL-6), IL-1β, IL-8, IL-10, monocyte chemoattractant protein-1 (MCP-1), GRO-α (Growth Related Oncogene-α) and matrix metal loproteinase-8 (MMP-8), but not always limited thereto.

Besides the cytokines herein, one or more markers selected from the group consisting of alpha-defensin, beta-defensin, neutrophil defensins (HNP 1-3), bactericidal/permeability-increasing protein (BPI), calprotectin (MRP8/14), surfactant protein-A, surfactant protein-D, mannan-bindinglectin, c-reactive protein, Pentraxin 3, scavenger receptors, C-type lectins, Toll-like receptor (TLR)-4, TLR-2, TLR-3, TLR-6, intracellular pattern recognition receptors (Nod1, Nod2, RIG-1, MDA-5), RAGE (receptor for advanced glycation endproduct), serum amyloid P component, serum amyloid A, complement factors, mannan-binding lectin, fibrinogen, prothrombin, factor VIII, von Willebrand factor, plasminogen, alpha 2-macroglobul in, ferritin, hepcidin, ceruloplasmin. haptoglobin, orosomucoid, alpha 1-antitrpysin, alpha 1-antichymotrypsin, lipopolysaccharide-binding protein (LBP), albumin, transferrin including lactoferrin), transthyretin, retinol-binding protein, antithrombin, transcortin, IL-1beta receptor antagonist, tumor necrosis factor (TNF)-alpha, IL-12, IL-16, IL-18, CSFs (colony-stimulating factors), epithelial cell-derived neutrophil-activating peptide-78 (ENA-78), regulated on activation normal T cell expressed and secreted [RANTES] CCL5, CXCL6 (granulocyte chemotactic protein-2), CXCL9 MIG, CXCL10: IP-10, CXCL11. CXCL13 [BCA-1], Exodus-1 [CCL20], MIF (macrophage migration inhibitory factor): MIP-1 alpha (CCL3), MIP-1beta (CCL4), CD11b, CD11c, CD13, CD15, CD66, CD14, CD64, CD66b, CD18, CD16, CD62L, CD67, HLA-DR, sHLA-G, Dihydroepiandrotendione (DHEA)-S, Cortisol, CRF (corticotrophin-releasing factor), CRF-binding protein, adrenocorticotropin, Urocortin, estriol, MMP-1, MMP-2, TIMP-2, MMP-3, MMP-7, MMP-9, arachidonate lipoxygenase metabolites, prostaglandins, prostacyclins, thromboxanes, leukotrienes, Catalase, Caspase-1 (NALP3 inflammasome), glucose, total hemoglobin, leptin, adiponectin, resistin, visfatin, Retinol binding protein 4 (RBP4), endotoxin, Epidermal growth factor (EGF), Insulin-like growth factor binding protein-1 (IGFBP-1) neutrophil elastase, leukocyte elastase (ELA2, neutrophil), SLPI (secretory leukocyte protease inhibitor), S100 calcium binding protein B, Heat shock protein, Endothel in-1, -2, Angiopoietin-2, Calcium-binding protein, Soluble Triggering receptor expressed on myeloid cells 1 (sTREM1), Protein-Z (vitamin K-dependent plasma glycoprotein), Tissue factor and Platelet activating factor (PAF) can be used.

According to the preferred embodiment of the present invention. 'inflammation and infection in amniotic fluid' was assessed in amniotic fluid collected by transabdominal amniocentesis and in amniotic fluid leaked through the cervix to vagina in patients with premature rupture of membranes. The concentrations of interleukin-6 (IL-6), IL-1β, IL-8, IL-10, monocyte chemoattractant protein-1 (MCP-1), GRO-α (Growth Related Oncogene-α) and matrix metal loproteinase-8 (MMP-8) were measured and compared. Infection in amniotic fluid was determined by positive culture of aerobic bacteria, anaerobic bacteria and genital mycoplasma, and inflammation in amniotic fluid was determined when the number of white blood cells in amniotic fluid was 19/mm$^2$ or higher.

As a result, when the cut-off values of IL-6 concentration was selected at 1 ng/ml, 1.5 ng/ml, 2.6 ng/ml and 10 ng/ml in amniotic fluid leaked through the cervix into the vagina in patients with premature rupture of membranes, IL-6 concentration in amniotic fluid leaked through the cervix into the vagina had sensitivity of 100, 85.7, 85.7 and 57.1% and specificity of 33.3, 50, 83.3 and 100%, respectively in diagnosing the 'inflammation or infection in amniotic fluid collected by transabdominal amniocentesis' (see FIG. 4 and Table 2).

Also, when the cut-off value of IL-8 concentration was selected at 1 ng/ml, 2 ng/ml, 3 ng/ml, 4 ng/ml and 10 ng/ml in amniotic fluid leaked through the cervix into the vagina in patients with premature rupture of membranes, IL-8 concentration in amniotic fluid leaked through the cervix into the vagina had sensitivity of 100, 100, 87.5, 75 and 75% and specificity of 40, 60, 70, 70 and 100%, respectively in diagnosing the 'inflammation or infection in amniotic fluid collected by transabdominal amniocentesis' (see FIG. 5 and Table 3).

Also, when the cut-off values of IL-1β concentration was selected at 100 pg/ml, 200 pg/ml, 500 pg/ml and 1000 pg/ml in amniotic fluid leaked through the cervix into the vagina in patients with premature rupture of membranes, IL-1β concentration in amniotic fluid leaked through the cervix into the vagina had sensitivity of 87.5, 87.5, 75.0 and 75.0% and specificity of 70.0, 70.0, 80.0 and 90.0%, respectively in diagnosing the 'inflammation or infection in amniotic fluid collected by transabdominal amniocentesis' (see FIG. 6 and Table 4).

Also, when the cut-off values of MCP-1 concentration was selected at 500 pg/ml, 1000 pg/ml, 1500 pg/ml, 2000 pg/ml and 2500 pg/ml in amniotic fluid leaked through the cervix into the vagina in patients with premature rupture of membranes. MCP-1 concentration in amniotic fluid leaked through the cervix into the vagina had sensitivity of 85.7, 85.7, 85.7, 71.4 and 57.1% and specificity of 22.2, 55.6, 66.7, 77.8 and 88.9% respectively for diagnosing the 'inflammation or infection in amniotic fluid collected by transabdominal amniocentesis' (see FIG. 7 and Table 5).

In addition, when the cut-off values of GRO-α concentration was selected at 250 pg/ml, 500 pg/ml, 1000 pg/ml and 5000 pg/ml in amniotic fluid leaked through the cervix into the vagina in patients with premature rupture of membranes, GRO-α concentration in amniotic fluid leaked through the cervix into the vagina had sensitivity of 57.1, 57.1, 57.1 and 42.9% and specificity of 44.4, 66.7, 77.8 and 100% respectively in diagnosing the 'inflammation or infection in amniotic fluid collected by transabdominal amniocentesis' (see FIG. 8 and Table 6).

However, when the cut-off values of IL-10 concentration was selected at 100 pg/ml and 150 pg/ml in amniotic fluid leaked through the cervix into the vagina in patients with premature rupture of membranes, IL-10 concentration in amniotic fluid leaked through the cervix into the vagina all had sensitivity of 25% and specificity of 100% in diagnosing the 'inflammation or infection in amniotic fluid collected by transabdominal amniocentesis' (see FIG. 9 and Table 7). Also, when the cut-off values of MMP-8 concentration was selected at 23 ng/ml, 50 ng/ml and 100 in amniotic fluid leaked through the cervix into the vagina in patients with premature rupture of membranes, MMP-8 concentration in amniotic fluid leaked through the cervix into the Vagina had sensitivity of 83.3, 66.7 and 66.7% and specificity of 16.7, 50 and 66.7% respectively in diagnosing the 'inflammation or infection in amniotic fluid collected by transabdominal amniocentesis' (see FIG. 10 and Table 8).

As a result, because the sensitivity and specificity of IL-10 and MMP-8 concentration in amniotic fluid leaked through the cervix into the vagina were low in diagnosing the 'inflammation or infection in amniotic fluid collected by transabdominal amniocentesis', IL-10 and MMP-8 were not suitable to be used as a marker to predict or diagnose the inflammation/infection in amniotic fluid.

In the amniotic fluid that is leaked through the cervix into the vagina, the concentration of one or more inflammatory markers selected from the group consisting of cytokine families IL-6, IL-1β, IL-8, MCP-1 and GRO-α have high sensitivity and specificity in the prediction or diagnosis of infect ion/inflammation in amniotic fluid. Therefore, measuring the amount of the above-mentioned cytokine enables the prediction or diagnosis of inflammation and/or infection in the amniotic fluid. In addition, the inflammatory marker selected from the group consisting of IL-6, IL-1β, IL-8, MCP-1 and GRO-α can be used alone or in combination for diagnosis.

The cytokine is selected from the group consisting of IL-6, IL-1β, IL-8, MCP-1 and GRO-α, but not limited thereto.

The amniotic fluid leaked through the cervix into the vagina in Step 1) can be collected with an amniotic fluid collecting apparatus. Any apparatus that can collect amniotic fluid leaked through the cervix into the vagina may be used, preferably a syringe, pipette, spoon, cotton swab, swab, Nelaton's catheter, or amniotic fluid collecting device which is foldably formed at the upper end of an amniotic fluid collecting bag for close contact with the external orifice of the cervix. The fluid can be collected more preferably by the amniotic collecting apparatus described in Korean Patent No. 10-0789849 or Korean Patent Application No. 2010-0031404.

The sample can be manipulated in order to increase detection sensitivity of an inflammatory marker. For example, the amniotic fluid sample leaked through the cervix into the vagina that is collected from the pregnant mother can be pretreated by ion exchange chromatography, affinity chromatography, size exclusion chromatography, liquid chromatography, sequential extraction or gel electrophoresis, etc. but not limited thereto.

The concentration of cytokines in Step 1) can be measured by two-dimensional gel electrophoresis, a biochip or an antibody that specifically binds to the cytokine. The biochip is preferably a protein chip or DNA array. In addition, the method using the antibody that specifically binds to the cytokine is selected from the group consisting of Western blot. ELISA (enzyme-Linked Immunosorbent assay), colorimetric method, electrochemical method, fluorimetric method, luminometry, particle counting method, visual assessment and scintillation counting method.

In Step 2), the cut-off value of inflammatory marker IL-6 as an inflammatory marker is 1 to 10 ng/ml, preferably 2.6 ng/ml; the cut-off value if of IL-8 is 1 to 30 ng/ml, preferably 10 ng/ml; the cut-off value of IL-1β is 100 to 1000 pg/ml, preferably 150 pg/ml; the cut-off value of MCP-1 is 500 to 2500 pg/ml, preferably 2000 pg/ml; and the cut-off value of GRO-α is 500 to 5000 pg/ml.

The present invention further provides a kit for predicting or diagnosis of inflammation or infection in amniotic fluid using amniotic fluid leaked through the cervix into the vagina, which includes an antibody binding specifically to above-mentioned inflammatory markers.

The marker herein is an inflammatory marker, preferably cytokine, and more preferably selected from the group consisting of interleukin-6 (IL-6), IL-1β, IL-8, IL-10, monocyte chemoattractant protein-1 (MCP-1), GRO-α (Growth Related Oncogene-α) and matrix metal loproteinase-8 (MMP-8), but not always limited thereto.

Besides the cytokines herein, one or more markers selected from the group consisting of alpha-defensin, beta-defensin, neutrophil defensins (HNP 1-3), bactericidal/permeability-increasing protein (BPI), calprotectin (MRP8/14), surfactant protein-A, surfactant protein-D, mannan-binding lectin, c-reactive protein, Pentraxin 3, scavenger receptors, Otype lectins. Toll-like receptor (TLR)-4, TLR-2, TLR-3. TLR-6, intracellular pattern recognition receptors (Nod1, Nod2, RIG-1, MDA-5), RAGE (receptor for advanced glycation endproduct), serum amyloid P component, serum amyloid A, complement factors, mannan-binding lectin, fibrinogen, prothrombin, factor VIII, von Willebrand factor, plasminogen, alpha 2-macroglobul in, ferritin, hepcidin, ceruloplasmin, haptoglobin, orosomucoid, alpha 1-antitrpysin, alpha 1-antichymotrypsin, lipopolysacchar i de-binding protein (LBP), albumin, transferrin including lactoferrin), transthyretin, retinol-binding protein, antithrombin, transcortin, IL-1beta receptor antagonist, tumor necrosis factor (TNF)-alpha, IL-12, IL-16, IL-18, CSFs (colony-stimulating factors), epithelial cell-derived neutrophil-activating peptide-78 (ENA-78), regulated on activation normal T cell expressed and secreted [RANTES]: CCL5, CXCL6 (granulocyte chemotactic protein-2), CXCL9: MIG, CXCL10: IP-10, CXCL11, CXCL13 [BCA-1], Exodus-1 [CCL20], MIF (macrophage migration inhibitory factor): MIP-1alpha (CCL3). MIP-1beta (CCL4), CD11b. CD11c, CD13. CD15. CD66, CD14, CD64, CD66b. CD18, CD16, CD62L, CD67, HLA-DR, sHLA-G, Dihydroepiandrotendione (DHEA)-S, cortisol CRF (corticotrophin-releasing factor). CRF-binding protein, adrenocorticotropin. Urocortin, estriol, MMP-1, MMP-2, TIMP-2, MP-3. MMP-7, MMP-9, arachidonate lipoxygenase metabolites, prostaglandins, prostacyclins, thromboxanes, leukotrienes, Catalase. Caspase-1 (NALP3 inflammasome), glucose, total hemoglobin, leptin, adiponectin, resistin, visfatin, Retinol binding protein 4 (RBP4), endotoxin, Epidermal growth factor (EGF). Insulin-like growth factor binding protein-1 (IGFBP-1), neutrophil elastase, leukocyte elastase (ELA2, neutrophil), SLPI (secretory leukocyte protease inhibitor), S100 calcium binding protein B, Heat shock protein, Endothelin-1, Angiopoietin-2, Calcium-binding protein. Soluble Triggering receptor expressed on myeloid cells 1

(sTREM1), Protein-Z (vitamin K-dependent plasma glycoprotein), Tissue factor and Platelet activating factor (PAF) can be used.

In a preferred embodiment of the present invention, the concentration of one or more inflammatory markers selected from the group consisting of IL-6, IL-1β, IL-8. MCP-1 and GRO-α amniotic fluid that was leaked through the cervix into the vagina and collected from patients with premature rupture of membranes had high sensitivity and specificity in the prediction or diagnosis of infection/inflammation in amniotic fluid. Therefore, measuring the amount of above-mentioned cytokine enables the prediction or diagnosis of inflammation and/or infection in the amniotic fluid.

The kit herein enables the medical practitioner such as doctors to predict or diagnose inflammation and/or infection in amniotic fluid by determining whether the amniotic fluid leaked through the cervix into the vagina has markers of inflammation and/or infection. In addition, the kit can be used to identify compounds that regulate the expression of one or more markers from amniotic fluid inflammation and/or infection model in vivo or ex vivo (e.g., mouse and rat animal models). As a result, the kit may further include the marker of the present invention as a standard material.

The antibody included in the kit can be a polyclonal antibody, a monoclonal antibody and a fragment being able to bind with an epitope, etc.

The monoclonal antibody can be prepared by any technique used for producing antibody molecule through continuous cell line culture, which is exemplified by hybridoma technique, human B-cell hybridoma technique, and EBV-hybridoma technique, but not always limited thereto (Kohler G et al., Nature 256:495-497, 1975; Kozbor D et al., J Immunol Methods 81:31-42, 1985; Cote R J et al., Proc Natl Acad Sci 80:2026-2030, 1983; and Cole S P et al., Mol Cell Biol 62:109-120, 1984).

The polyclonal antibody can be prepared by the conventional processes of injecting one of the markers into an animal, drawing blood from the animal and obtaining serum containing the antibody from the blood sample. Such polyclonal antibody can be purified by any conventional method known to those in the art and be produced by using any animal model, including goat, rabbit, sheep, monkey, horse, pig, cow, dog and mouse as a host.

Also, an antibody fragment that harbors the specific binding site bound to one of the markers can be prepared. For example, F(ab')2 fragment can be prepared by decomposing an antibody molecule with pepsin. Fab fragment can be prepared by reducing the disulfide bridge of F(ab')2. In addition, Fab expression library can be constructed, by which a specific monoclonal Fab fragment can be identified fast and easy (Huse W D et al., Science 254: 1275-1281, 1989).

The antibody can be fixed on a solid substrate to make washing or conjugate separation process easy. The solid substrate is exemplified by synthetic resin, nitrocellulose, glass plate, metal plate, glass fiber, microspheres and microbeads. The synthetic resin herein is exemplified by polyester, polyvinyl chloride, polystyrene, polypropylene. PVDF and nylon.

In the case that a sample obtained from a patient is put into contact with the marker protein specific antibody fixed on a solid substrate, the sample can be diluted properly before the contact.

The kit of the present invention also includes a detector that is specifically bound to the marker antibody. The detector can be a conjugate labeled with a chromogenic enzyme, a fluorescent material, a radioisotope or a colloid, and a secondary antibody specifically binding to the cytokine antibody is preferred. The chromogenic enzyme is exemplified by peroxidase, alkaline phosphatase or acid phosphatase (e.g., horseradish peroxidase); and the fluorescent material is exemplified by fluorescein carboxylic acid (FCA), fluorescein isothiocyanate (FITC), fluorescein thiourea (FTH), phycoerythrin (PE), 7-acetoxycoumarin-3-yl, fluorescein-5-yl, fluorescein-6-yl, 2',7'-dichloro fluorescein-5-yl, 2',7'-dichloro fluorescein-6-yl, dihydrotetramethylrhodamine-4-yl, tetramethylrhodamine-5-yl, tetramethyl rhodamine-6-yl, 4,4-difluoro-5,7-dimethyl-4-bora-3a,4a-diaza-s-indacen-3-ethyl, 4,4-difluoro-5,7-diphenyl-4-bora-3 or 4a-diaza-s-indacene-3-ethyl, but not always limited thereto.

The kit of the present invention is suitable for diagnosis of inflammation and/or infection in amniotic fluid by measuring the antigen-antibody reactions of the antigen-antibody complex or by measuring the amount of detector after treating the antigen-antibody complex with the detector. Examples of antigen-antibody reactions are ELISA method, immunoprecipitation method, immunofluorescence method, enzyme-substrate chromogenic method, antigen-antibody aggregation method. Quantification or detection of the detector can be performed by using chromogen, fluorescence, iluminescence, chemiluminescence, optical density, reflection or transmission.

High throughput screening (FITS) system is preferably used for screening the amount of the detector. For the system, a method for detecting the chromogenic reaction by adding a substrate that induces the color development of the chromogenic enzyme bound to the detector; fluorescence assay performed by measuring fluorescence from the fluorescein labeled detector or radio assay performed by measuring radiation from the isotope labeled detector; SP (surface plasmon resonance) measuring changes of plasmon resonance on the surface without using a detector or SPRI (surface plasmon resonance imaging) method which detects the SPR system by imaging can be preferably used, but not always limited thereto.

The chromogenic substrate can be used according to the chromogenic enzyme, which is exemplified by TMB (3,3',5,5'-tetramethyl bezidine), ABTS [2,2'-azino-bis(3-ethylbenzothiazoline-6-sulfonic acid)], and OPD (o-phenylenediamine), etc. At this time, the chromogenic substrate is preferably provided as dissolved in buffer (0.1M NaOAc, pH 5.5). Chromogenic substrate such as TMB is degraded by the chromogenic substrate linked to the detector and forms chromogenic precipitates. The existence of cytokine can be detected by confirming the amount of chromogenic precipitation through visual observation. Also, the fluorescence method detects the signal by spotting the fluorescence labeled detector and using fluorescence scanning program. The level of binding can be confirmed by this method.

Unlike fluorescence assay. SPR system facilitates real time analysis of the level of antibody binding since it is unnecessary to label the sample with a fluorescent material. However, this method is disadvantageous for simultaneous large scale analysis. SPRI enables simultaneous large scale analysis of samples using microarray but has a disadvantage of low detection sensitivity.

Also, the kit of the present invention may additionally include washing solution or eluent to remove the residual materials after antigen-antibody conjugation reaction and binding reaction of detectors. The washing solution herein preferably includes phosphate buffer, NaCl and Tween 20, and is more preferably the buffer (PBST) composed of 0.02 M phosphate buffer, 0.13 M NaCl, and 0.05% Tween 20, but not always limited thereto. The washing solution is added to the fixture after the reaction of detector with the antigen-antibody conjugate, followed by washing 3-6 times, but not always limited thereto. The reaction terminating solution is preferably sulfuric acid solution ($H_2SO_4$), but not always limited thereto.

The sample that is used for analysis is amniotic fluid leaked through the cervix into the vagina in pregnant woman with premature rupture of membranes. The amniotic fluid herein can be collected with a noninvasive amniotic fluid collecting apparatus. Any apparatus that can collect amniotic fluid leaked through the cervix into vagina may be used, preferably a syringe, pipette, spoon, cotton swab, swab, Nelaton's catheter, or amniotic fluid collecting device which is foldably formed at the upper end of an amniotic fluid collecting bag for close contact with the external orifice of the cervix. The amniotic fluid can be collected more preferably by the amniotic collecting apparatus described in Korean Patent No. 10-0789849 or Korean Patent Application No. 2010-0031404. The sample can be manipulated in order to increase detection sensitivity of an inflammatory marker. For example, the amniotic fluid sample leaked through the cervix into vagina is collected from the pregnant mother, can be pretreated by ion exchange chromatography, affinity chromatography, size exclusion chromatography, liquid chromatography, sequential extraction or gel electrophoresis, etc, but not limited thereto.

Until now, there has been no report using the cytokines selected in the present invention to diagnose the onset and progression of inflammation or infection in the amniotic fluid leaked through the cervix as diagnostic markers for inflammation and/or infection in amniotic fluid. Therefore, the present invention is the first report using the above-mentioned cytokine as an inflammatory marker.

In addition, as the cytokine herein can be detected from the amniotic fluid leaked through the cervix into vagina, unlike the conventional markers, it does not cause discomfort in patients and can be applied as a noninvasive method for diagnosing inflammation and/or infection in the amniotic fluid.

The present invention further provides a biochip for predicting or diagnosis of inflammation or infection in the amniotic fluid using amniotic fluid leaked through the cervix into the vagina, in which biomolecules binding specifically to above-mentioned inflammatory' markers are integrated to a sol id substrate.

The marker is an inflammatory marker, preferably a cytokine, and more preferably one selected from the group consisting of interleukin-6 (IL-6), IL-1β, IL-8, IL-10, monocyte chemoattractant protein-1 (MCP-1). GRO-α (Growth Related Oncogene-α) and matrix metal loproteinase-8 (MMP-8), but not always limited thereto.

Besides the cytokines herein, one or more markers selected from the group consisting of alpha-defensin, beta-defensin, neutrophil defensins (HNP 1-3), bactericidal/permeability-increasing protein (BPI), calprotectin (MRP8/14), surfactant protein-A, surfactant protein-D, mannan-binding lectin, c-reactive protein. Pentraxin 3, scavenger receptors, C-type lectins, Toll-like receptor (TLR)-4, TLR-2, TLR-3, TLR-6, intracellular pattern recognition receptors (Nod1, Nod2, RIG-1, MDA-5), RAGE (receptor for advanced glycation endproduct), serum amyloid P component, serum amyloid A, complement factors, mannan-binding lectin, fibrinogen, prothrombin, factor VIII, von Willebrand factor, plasminogen, alpha 2-macroglobul in, ferritin, hepcidin, ceruloplasmin, haptoglobin, orosomucoid, alpha 1-antitrpysin, alpha 1-antichymotrypsin, lipopolysaccharide-binding protein (LBP), albumin, transferrin including lactoferrin), transthyretin, retinol-binding protein, ant 1 thrombin, transcortin, IL-1beta receptor antagonist, tumor necrosis factor (TNF)-alpha, IL-12, IL-16 IL-18, CSFs (colony-stimulating factors), epithelial cell-derived neutrophil-activating peptide-78 (ENA-78), regulated on activation normal T cell expressed and secreted [RANTES]: CCL5. CXCL6 (granulocyte chemotactic protein-2). CXCL9: MIG, CXCL10: IP-10, CXCL11, CXCL13 [BCA-1]. Exodus-1 [CCL20], MIF (macrophage migration inhibitory factor): MIP-1alpha (CCL3) MIP-1beta (CCL4), CD11b. CD11c. CD13, CD15, CD66, CD14, CD64, CD66b, CD18, CD16, CD62L, CD67, HLA-DR, sHLA-G, Dihydroepiandrotendione (DHEA)-S, cortisol, CRF (corticotrophin-releasing factor), CRF-binding protein, adrenocorticotropin, Urocortin, estriol, MMP-1, MMP-2. TIMP-2. MMP-3, MMP-7, MMP-9, arachidonate lipoxygenase metabolites, prostaglandins, prostacyclins, thromboxanes, leukotrienes Catalase, Caspase-1 (NALP3 inflammasome) glucose, total hemoglobin, leptin, adiponectin, resistin, visfatin. Retinol binding protein 4 (RBP4), endotoxin, Epidermal growth factor (EGF), Insulin-like growth factor binding protein-1 (IGFBP-1), neutrophil elastase, leukocyte elastase (ELA2, neutrophil), SLPI (secretory leukocyte protease inhibitor), S100 calcium binding protein B, Heat shock protein, Endothel in-1, -2, Angiopoietin-2, Calcium-binding protein. Soluble Triggering receptor expressed on myeloid cells 1 (sTREM1), Protein-ZCvitamin-dependent plasma glycoprotein). Tissue factor and Platelet activating factor (PAF) can be used.

In a preferred embodiment of the present invention, the concentration of one or more inflammatory markers selected from the group consisting of IL-6, IL-1β, IL-8, IL-10, MCP-1 and GRO-α in amniotic fluid that was leaked from the cervix into the vagina in patients with premature rupture of membranes had a high sensitivity and specificity in the prediction or diagnosis of infection/inflammation in amniotic fluid. Therefore, measuring the amount of the above-mentioned cytokine enables the prediction or diagnosis of inflammation and/or infection in the amniotic fluid.

In order to use the biochip of the present invention for measuring the markers for prediction or diagnosis of inflammation and/or infection in amniotic fluid in patients with premature rupture of membranes with positive inflammation and/or infection in the amniotic fluid, the biochip may include an antibody that specifically binds to the marker, or may include a combination of the two types of antibodies.

The biomolecule herein is selected from the group consisting of low molecular weight compound, ligand, aptamer, peptide, polypeptide, specific binding protein, high molecular weight compound and antibody, and any molecule that specifically binds to the marker can be used. The biomolecule herein is preferably an antibody or an aptamer, but not always limited thereto.

The antibody used herein is preferably polyclonal antibody or monoclonal antibody, more preferably monoclonal antibody can be used. The antibody that specifically binds to the marker can be produced by a conventional method well-known to those in the art, or commercially available antibody can be purchased for use. The antibody can be produced by the conventional method of injecting the antigenic protein to an outside host. The outside host may include mammalian animals such as mouse, rat, sheep and rabbit. The immunogen can be administered via intramuscular, intraperitoneal or subcutaneous injection method. In general, adjuvant can be co-injected to increase the antigenicity. Blood is drawn from the host animal regularly and serum showing peak titer and specificity against antigen is obtained for antibody isolation.

The solid substrate herein is selected from the group consisting of plastic, glass, metal and silicon and preferably the solid substrate is chemically treated or fixed with linker molecule to attach the antibody, but not always limited thereto. The biochip herein collects the whole protein from the sample to react with the biochip, which enables easy and accurate prediction or diagnosis of inflammation and/or infection in the amniotic fluid.

The active group coated on the solid substrate functions to bind the molecules, and is selected from the group consisting of amine group, aldehyde group, carboxyl group and thiol group. All functional groups well-known to those in the art to bind the protein molecule on the solid substrate may be used, but not limited thereto.

The sample used herein for analysis is amniotic fluid leaked through the cervix into vagina in pregnant woman with premature rupture of membranes. The amniotic fluid herein can be collected with a noninvasive amniotic fluid collecting apparatus. Any apparatus that can collect amniotic fluid leaked through the cervix into vagina may be used, preferably a syringe, pipette, spoon, cotton swab, swab, Nelaton's catheter, or amniotic fluid collecting device which is foldably formed at the upper end of an amniotic fluid collecting bag for close contact with the external orifice of the cervix. The amniotic fluid can be more preferably collected by the amniotic collecting apparatus described in Korean Patent No. 10-0789849 or Korean Patent Application No. 2010-0031404.

The sample can be manipulated in order to increase detection sensitivity of an inflammatory marker. For example, the amniotic fluid sample leaked through the cervix into the vagina and collected from the pregnant mother can be pretreated by ion exchange chromatography, affinity chromatography, size exclusion chromatography, liquid chromatography, sequential extraction or gel electrophoresis, etc. but not limited thereto.

The present invention further provides a kit for predicting or diagnosis of inflammation or infection in amniotic fluid, using amniotic fluid leaked through the cervix into the vagina.

In addition, the present invention provides a biochip for predicting or diagnosis of inflammation or infection in amniotic fluid, using amniotic fluid leaked through the cervix into vagina.

In a preferred embodiment of the present invention, the concentration of one or more inflammatory markers selected from the group consisting of IL-6, IL-1β, IL-8, IL-10, MCP-1 and GRO-α in amniotic fluid that was leaked through the cervix into the vagina in patients with premature rupture of membranes had a high sensitivity and specificity in the prediction or diagnosis of infection/inflammation in amniotic fluid. Therefore, measuring the expression amount of the cytokine enables the prediction or diagnosis of inflammation and/or infection in the amniotic fluid.

Practical and presently preferred embodiments of the present invention are illustrative as shown in the following Examples.

However, it will be appreciated that those skilled in the art, on consideration of this disclosure, may make modifications and improvements within the spirit and scope of the present invention.

MODE FOR INVENTION

Example 1

Using IL-6 for Measuring Inflammation and/or Infection in Amniotic Fluid

<1-1> Study Subject

Amniotic fluid obtained by abdominal amniocentesis and amniotic fluid leaked from cervix into the vagina were collected from 18 pregnant mothers with premature rupture of membranes. The concentration of IL-6 was measured and compared by performing ELISA analysis on the above collected amniotic fluids using antibody against IL-6 (R&D system, Minneapolis, Minn.).

<1-2> Definition of ˹ Infection and Inflammation in Amniotic Fluid˼

'Infection and inflammation in amniotic fluid' is defined by culturing aerobic and anaerobic bacteria and genital mycoplasmas and by counting the number of white blood cells in the amniotic fluid collected by abdominal amniocentesis. In 'infection and inflammation in amniotic fluid', amniotic fluid infection is defined by the culture of aerobic bacteria, anaerobic bacteria and genital mycoplasma in the amniotic fluid, and amniotic fluid inflammation is defined when the number of white blood cells in amniotic fluid is higher than 19 cells/mm$^5$ (Park J S. Yoon B H et al., Am J Obstet Gynecol 185:1156-1161, 2001; Yoon B H et al., Am J Obstet Gynecol 182:675-681, 2000).

As a result, the concentration of IL-6 indicating inflammation and/or infection in amniotic fluid in patients with premature rupture of membranes was defined as 2.6 ng/ml. In the case of amniotic fluid collected by transabdominal amniocentesis showing 'inflammation or infection', 5 out of 7 cases showed IL-6 level higher than 2.6 ng/ml, in amniotic fluid collected by transabdominal amniocentesis, while 6 out of 7 cases showed IL-6 level higher than 2.6 ng/ml in the group of amniotic fluid leaked through the cervix into the vagina. That is, when the cut-off value of IL-6 was set at 2.6 ng/ml, in amniotic fluid leaked through the cervix into the vagina from the group of pregnant women with positive 'inflammation or infection', 6 out of 7 cases showed IL-6 level higher than 2.6 ng/ml, indicating sensitivity of 83.3%. In the group of pregnant women whose amniotic fluid collected by transabdominal amniocentesis showed negative 'inflammation or infection', 5 out of 6 patients showed IL-6 level lower than cut-off value, indicating specificity of 85.7%. As a result, when the cut-off values of IL-6 concentration was selected at 1 ng/ml, 1.5 ng/ml, 2.6 ng/ml and 10 ng/ml in amniotic fluid leaked through the cervix into the vagina in patients with premature rupture of membranes, IL-6 concentration in amniotic fluid leaked through the cervix into the vagina had sensitivity of 100, 85.7, 85.7 and 57.1% and specificity of 33.3, 50, 83.3 and 100%, respectively for diagnosing the 'inflammation or infection in amniotic fluid collected by transabdominal amniocentesis' (see FIG. 4 and Table 2).

<1-3> Correlation Between Amniotic Fluid from Transabdominal Amniocentesis and Amniotic Fluid Leaked Through the Cervix into the Vagina When the cut-off value of IL-6 was set at 2.6 ng/ml in amniotic fluid leaked from the cervix into the vagina, of the 7 cases with amniotic fluid infection/inflammation, 6 cases showed values higher than the cut-off value, indicating sensitivity' of 85.7% and only 1 case with amniotic fluid infection/inflammation was not diagnosed. In addition, in this case, in 6 cases without amniotic fluid infection/inflammation, 5 cases showed value lower than cut-off value, showing specificity of 83.3%, and only 1 case was not diagnosed.

The concentration of IL-6 measured in amniotic fluid leaked through the cervix into the vagina shows high sensitivity and specificity for prediction and diagnosis of infection/inflammation in amniotic fluid, and therefore may be used as a prediction and diagnosis marker for infection/inflammation in amniotic fluid.

TABLE 2

Sensitivity and specificity in predicting infection/inflammation
in amniotic fluid according to each of the cut-off value of IL-6 in the
amniotic fluid leaked through the cervix into vagina.

| Cut-off Concentration (ng/ml) | Sensitivity | Specificity |
|---|---|---|
| 1 | 100% (7/7) | 33.3% (2/6) |
| 1.5 | 85.7% (6/7) | 50.0% (3/6) |
| 2.6 | 85.7% (6/7) | 83.3% (6/6) |
| 10 | 57.1% (4/7) | 100% (6/6) |

TABLE 3

Sensitivity and specificity in predicting infection/inflammation
in amniotic fluid according to each of the cut-off value of IL-8 in the
amniotic fluid leaked through the cervix into the vagina.

| Cut-off Concentration (ng/ml) | Sensitivity | Specificity |
|---|---|---|
| 1 | 100% (8/8) | 40.0% (4/10) |
| 2 | 100% (8/8) | 60.0% (6/10) |
| 3 | 87.5% (7/8) | 70.0% (7/10) |
| 4 | 75.0% (6/8) | 70.0% (7/10) |
| 10 | 75.0% (6/8) | 100% (10/10) |

Example 2

Using IL-8 for Measuring Inflammation and/or Infection in Amniotic Fluid

<2-1> Analysis of Inflammation and/or Infection in Amniotic Fluid from Transabdominal Amniocentesis and Amniotic Fluid Leaked Through the Cervix into the Vagina By using the test subjects from Example <1-1>, the concentration of IL-8 was measured by ELISA analysis using 2 pg/ml of co-antibody-human IL-8 monoclonal anti body (Pierce endogen) and 0.05 ug/ml of biotinylated detecting antibody-anti-human IL-8 monoclonal antibody (pierce endogen). 'Infection and inflammation in amniotic fluid' was determined by the method of Example <1-2>.

As a result, the concentration of IL-8 indicating inflammation and/or infection in amniotic fluid in patients with premature rupture of the membrane was defined as 6 ng/ml. Eight patients were confirmed as positive for 'inflammation or infection' in amniotic fluid collected by transabdominal amniocentesis. Out of these patients, 6 patients showed 6 ng/ml or higher concentration of IL-8 in the amniotic fluid that was leaked from the cervix to vagina. Therefore, the cut-off values of IL-8 concentration was selected at 1 ng/ml, 2 ng/ml, 3 ng/ml, 4 ng/ml and 10 ng/ml in amniotic fluid leaked through the cervix to vagina in patients with premature rupture of membranes, IL-8 concentration in amniotic fluid leaked through the cervix into the vagina had sensitivity of 100, 100, 87.5, 75 and 75% and specificity of 40, 60, 70, 70 and 100%, respectively, for diagnosing the 'inflammation or infection in amniotic fluid collected by transabdominal amniocentesis' (see FIG. 5 and Table 3).

<2-2> Correlation Between Amniotic Fluid from Transabdominal Amniocentesis and Amniotic Fluid Leaked Through the Cervix into the Vagina When the cut-off value of IL-8 was determined as 10 ng/ml in amniotic fluid leaked from the cervix to vagina, out of 8 cases with amniotic fluid infection/inflammation, 6 cases showed values higher than the cut-off value, indicating sensitivity of 75.0% and 2 cases with amniotic fluid infection/inflammation was not diagnosed. In addition, in this case, all of the 10 cases without amniotic fluid infection/inflammation showed values lower than the cut-off value, showing specificity of 100%, which indicates that all cases without amniotic fluid infection/inflammation were diagnosed.

Thus, the concentration of IL-8 measured in amniotic fluid leaked through the cervix into the vagina has high sensitivity and specificity for the prediction and diagnosis of infection/inflammation in amniotic fluid, and therefore may be used as a prediction and diagnosis marker for infection/inflammation in amniotic fluid.

Example 3

Using IL-ID for Measuring Inflammation and/or Infection in Amniotic Fluid

<3-1> Analysis of Inflammation and/or Infection in Amniotic Fluid from Transabdominal Amniocentesis and Amniotic Fluid Leaked Through the Cervix into the Vagina By using the test subjects from Example <1-1>, the concentration of IL-1β was measured by ELISA analysis using Douset ELISA development system, human IL-1 beta/IF2 (R&D), and 'infection and inflammation in amniotic fluid' was determined by the method of Example <1-2>.

As a result, the concentration of IL-1β indicating inflammation and/or infection in amniotic fluid in patients with premature rupture of membranes was defined as 200 pg/ml. Out of the eight patients who were confirmed as positive for 'inflammation or infection' in amniotic fluid collected by transabdominal amniocentesis, 7 patients showed 200 pg/ml or higher concentration of IL-1β in the amniotic fluid that was leaked from the cervix to vagina. Therefore, when the cut-off values of IL-1β concentration was selected at 100 pg/ml, 200 pg/ml, 500 pg/ml and 1000 pg/ml in amniotic fluid leaked through the cervix to vagina in patients with premature rupture of membranes, IL-β concentration in amniotic fluid leaked through the cervix into the vagina had a sensitivity of 87.5, 87.5, 75.0 and 75.0% and specificity of 70.0, 70.0, 80.0 and 90.0%, respectively for diagnosing the 'inflammation or infection in amniotic fluid collected by transabdominal amniocentesis' (see FIG. 6 and Table 4).

<3-2> Correlation Between Amniotic Fluid from Transabdominal Amniocentesis and Amniotic Fluid Leaked Through the Cervix into the Vagina When the cut-off value of IL-1 was determined as 150 pg/ml for amniotic fluid leaked from the cervix to vagina, out of 8 cases which showed positive infection/inflammation in amniotic fluid, 7 cases showed values higher than the cut-off, indicating sensitivity of 87.5% and only 1 case with amniotic fluid infection/inflammation was not diagnosed. In addition, among 10 cases without amniotic fluid infection/inflammation, 7 cases showed values lower than the cut-off, indicating specificity of 70.0%, and 3 cases without infection/inflammation in amniotic fluid were not diagnosed.

Thus, the concentration of IL-β measured in amniotic fluid leaked through the cervix into the vagina has high sensitivity and specificity for prediction and diagnosis of infection/inflammation in amniotic fluid, and therefore may be used as a prediction and diagnosis marker for infection/inflammation in amniotic fluid.

TABLE 4

Sensitivity and specificity in predicting infection/inflammation in amniotic fluid according to each of the cut-off value of IL-1β in the amniotic fluid leaked through the cervix into the vagina.

| Cut-off Concentration (pg/ml) | Sensitivity | Specificity |
|---|---|---|
| 100 | 87.5% (7/8) | 70.0% (7/10) |
| 150 | 87.5% (7/8) | 70.0% (7/10) |
| 500 | 75.0% (7/8) | 80.0% (8/10) |
| 1000 | 75.0% (7/8) | 90.0% (9/10) |

Example 4

Using MCP-1 for Measuring Inflammation and/or Infection in Amniotic Fluid

<4-1> Analysis of Inflammation and/or Infection in Amniotic Fluid from Transabdominal Amniocentesis and Amniotic Fluid Leaked Through the Cervix into the Vagina The concentration of MCP-1 was measured by ELISA analysis using Human CCL2/MCP-1 immunoassay, Quantikine (R&D system) from the test subjects of Example <1-1>, and then 'infection and inflammation in amniotic fluid' was determined according to the method of Example <1-2>.

As a result, the concentration of MCP-1 indicating inflammation and/or infection in amniotic fluid in patients with premature rupture of membranes was defined as 1.500 pg/ml. Out of the 7 patients who were positive for 'inflammation or infection' in amniotic fluid collected by transabdominal amniocentesis, 6 patients showed a concentration of MCP-1 higher than 1,500 pg/ml in the amniotic fluid leaked through the cervix to vagina. Therefore, when the cut-off values of MCP-1 concentration was selected at 500 pg/ml, 1000 pg/ml, 1500 pg/ml, 2000 pg/ml and 2500 pg/ml in amniotic fluid leaked through the cervix into the vagina in patients with premature rupture of membranes, MCP-1 concentration in amniotic fluid leaked through the cervix into the vagina had sensitivity of 85.7, 85.7, 85.7, 71.4 and 57.1% and specificity of 22.2, 55.6, 66.7, 77.8 and 88.9% respectively for diagnosing the 'inflammation or infection in amniotic fluid collected by transabdominal amniocentesis' (see FIG. 7 and Table 5).

<4-2> Correlation Between Amniotic Fluid from Transabdominal Amniocentesis and Amniotic Fluid Leaked Through the Cervix into the Vagina When the cut-off value of MCP-1 in the amniotic fluid leaked from the cervix to vagina was set at 2000 pg/ml, 5 cases out of 7 cases with infect ion/inflammation in amniotic fluid showed levels higher than the cut off value, indicating sensitivity of 71.4% and only 2 cases with infect ion/inflammation in amniotic fluid were not diagnosed. In addition, among 9 cases without amniotic fluid infect ion/inflammation, 7 cases showed values lower than the cut-off, indicating a specificity of 77.8%, and 2 cases without infect ion/inflammation in amniotic fluid were not diagnosed.

Thus, the concentration of MCP-1 measured in amniotic fluid leaked through the cervix into the vagina has high sensitivity and specificity for prediction and diagnosis of infection/inflammation in amniotic fluid, and therefore may be used as a prediction and diagnosis marker for infect ion/inflammation in amniotic fluid.

TABLE 5

Sensitivity and specificity in predicting infect ion/inflammation in amniotic fluid according to each of the cut-off value of MCP-1 in the amniotic fluid leaked through the cervix into the vagina.

| Cut-off Concentration (pg/ml) | Sensitivity | Specificity |
|---|---|---|
| 500 | 85.7% (6/7) | 22.2% (2/9) |
| 1000 | 85.7% (6/7) | 55.6% (5/9) |
| 1500 | 85.7% (6/7) | 66.7% (6/9) |
| 2000 | 71.4% (5/7) | 77.8% (7/9) |
| 2500 | 57.1% (4/7) | 88.9% (8/9) |

Example 5

Using GRO-α for Measuring Inflammation and/or Infection in Amniotic Fluid

<5-1> Analysis of Inflammation and/or Infection in Amniotic Fluid from Transabdominal Amniocentesis and Amniotic Fluid Leaked Through the Cervix into the Vagina The concentration of GRO-α was measured by ELISA analysis using Human CXCL1/GRO-alpha immunoassay, Quantikine (R&D system) from the test subjects of Example <1-1>, and then 'infection and inflammation in amniotic fluid' was determined according to the method of Example <1-2>.

As a result, the concentration of GRO-α indicating inflammation and/or infection in amniotic fluid in patients with premature rupture of membranes was set as 1000 pg/ml. Out of the 7 patients who were positive for 'inflammation or infection' in amniotic fluid collected by transabdominal amniocentesis, 4 patients showed a concentration of GRO-α higher than 1000 pg/ml in the amniotic fluid that was leaked through the cervix into the vagina in patients with premature rupture of membranes. GRO-α concentration in amniotic fluid leaked through the cervix into the vagina had sensitivity of 57.1, 57.1, 57.1 and 42.9% and specificity of 44.4, 66.7, 77.8 and 100% respectively in diagnosing the 'inflammation or infection in amniotic fluid collected by transabdominal amniocentesis'.

<5-2> Correlation Between Amniotic Fluid from Transabdominal Amniocentesis and Amniotic Fluid Leaked Through the Cervix into the Vagina When the cut-off value of GRO-α in the amniotic fluid leaked through the cervix into the vagina was set at 5000 pg/ml, 3 cases out of 7 cases with infection/inflammation in amniotic fluid showed levels higher than the cut off value, indicating sensitivity of 42.9% and 4 case with amniotic fluid infection/inflammation was not diagnosed. In addition, among 9 cases without amniotic fluid infection/inflammation, 9 cases showed values lower than the cut-off, indicating a specificity of 100%, and none of cases without infection/inflammation in the amniotic fluid were undiagnosed.

Thus, the concentration of GRO-α measured in amniotic fluid leaked through the cervix into the vagina has high specificity and not so low sensitivity, therefore may be used as a prediction and diagnosis marker for infection/inflammation in amniotic fluid.

TABLE 6

Sensitivity and specificity in predicting infection/inflammation in amniotic fluid according to each of the cut-off value of GRO-α in the amniotic fluid leaked through the cervix into the vagina.

| Cut-off Concentration (pg/ml) | Sensitivity | Specificity |
|---|---|---|
| 250 | 57.1% (4/7) | 44.4% (4/9) |
| 500 | 57.1% (4/7) | 66.7% (6/9) |
| 1000 | 57.1% (4/7) | 77.8% (7/9) |
| 5000 | 42.9% (3/7) | 100% (9/9) |

Comparative Example 1

Using IL-10 for Measuring Inflammation and/or Infection in Amniotic Fluid

<1-1> Analysis of Inflammation and/or Infection in Amniotic Fluid from Transabdominal Amniocentesis and Amniotic Fluid Leaked Through the Cervix into the Vagina The concentration of IL-10 was measured by ELISA analysis using 2 μg/ml of co-antibody-anti-human IL-10 monoclonal antibody (endogen) and 0.5 μg/ml of detecting antibody-biotinylated rat anti-human and viral IL-10 monoclonal antibody (Pharmingen) from the test subjects of Example <1-1>, and then 'infection and inflammation in amniotic fluid' was determined according to the method of Example <1-2>.

As a result, the concentration of IL-10 indicating inflammation and/or infection in amniotic fluid in patients with premature rupture of membranes was set as 150 pg/ml. Out of the 8 patients who were positive for 'inflammation or infection' in amniotic fluid collected by transabdominal amniocentesis, 2 patients showed a concentration of IL-10 higher than 150 pg/ml in the amniotic fluid that was leaked through the cervix into the vagina. Therefore, in amniotic fluid that was leaked through the cervix into the vagina, the cut-off values of IL-10 concentration (pg/ml) at 100 and 150 both showed sensitivity of 25% and specificity of 100%, respectively for diagnosing 'inflammation or infection in amniotic fluid' collected by transabdominal amniocentesis <1-2> Relationship Between Amniotic Fluid from Transabdominal Amniocentesis and Amniotic Fluid Leaked Through the Cervix into the Vagina When the cut-off value of IL-10 in the amniotic fluid leaked through the cervix to vagina was set at 150 pg/ml or higher, 2 cases out of 8 with infection/inflammation in amniotic fluid showed values higher than the cut off value, indicating sensitivity of 25.0% and 6 case with amniotic fluid infect ion/inflammation was not diagnosed. In addition, among 10 cases without amniotic fluid infection/inflammation, all 10 cases showed values lower than the cut-off, indicating a specificity of 100%, and none of cases without infection/inflammation in the amniotic fluid were undiagnosed.

TABLE 7

Sensitivity and specificity in predicting infection/inflammation in amniotic fluid according to each of the cut-off value of IL-10 in the amniotic fluid leaked through the cervix into the vagina.

| Cut-off Concentration (pg/ml) | Sensitivity | Specificity |
|---|---|---|
| 100 | 25.0% (2/8) | 100% (10/10) |
| 150 | 25.0% (2/8) | 100% (10/10) |

Comparative Example 2

Using MMP-8 for Measuring Inflammation and/or Infection in Amniotic Fluid

<2-1> Analysis of Inflammation and/or Infection in Amniotic Fluid from Transabdominal Amniocentesis and Amniotic Fluid Leaked Through the Cervix into the Vagina The concentration of MMP-8 was measured by ELISA analysis using MMP-8 antibody (Amersham Pharmacia Biotech, Inc Little Chalfont, Bucks, UK) from the test subjects of Example <1-1>, and then 'infection and inflammation in amniotic fluid' was determined according to the method of Example <1-2>.

As a result, the concentration of MMP-8 indicating inflammation and/or infection in amniotic fluid in patients with premature rupture of membranes was set as 23 ng/ml. Out of the 6 patients who were positive for 'inflammation or infection' in amniotic fluid collected by transabdominal amniocentesis, 5 patients showed a concentration of MMP-8 higher than 23 ng/ml in the amniotic fluid that was leaked from the cervix to vagina. Therefore, in amniotic fluid that was leaked through the cervix into the vagina, the cut-off values of MMP-8 concentration at 23 ng/ml, 50 ng/ml and 100 ng/ml showed sensitivity of 83.3, 66.7 and 66.7% and specificity' of 16.7, 50 and 66.7%, respectively for diagnosing 'inflammation or infection in amniotic fluid' collected by transabdominal amniocentesis <2-2> Relationship Between Amniotic Fluid from Transabdominal Amniocentesis and Amniotic Fluid Leaked Through the Cervix into the Vagina When the cut-off value of MMP-8 in the amniotic fluid leaked from the cervix to vagina was set at 23 ng/ml or higher, 5 cases out of 6 cases with infect ion/inflammation in amniotic fluid showed values higher than the cut off value, indicating sensitivity of 83.3% and only 1 case with amniotic fluid infect ion/inflammation was not diagnosed. However, in this case, among 6 cases without amniotic fluid infect ion/inflammation, only 1 case showed values lower than the cut-off, indicating a specificity of 16.7%, and 5 cases without infection/inflammation in the amniotic fluid were undiagnosed.

TABLE 8

Sensitivity and specificity in predicting infect ion/inflammation in amniotic fluid according to each of the cut-off value of MMP-8 in the amniotic fluid leaked through the cervix into the vagina.

| Cut-off Concentration (ng/ml) | Sensitivity | Specificity |
|---|---|---|
| 23 | 83.3% (5/6) | 16.7% (1/6) |
| 50 | 66.7% (4/6) | 50.0% (3/6) |
| 100 | 66.7% (4/6) | 66.7% (4/6) |

The invention claimed is:

1. A method for prediction or diagnosis of intra-amniotic inflammation or infection in a pregnant female subject comprising:
   1) measuring in a sample of amniotic fluid leaked through the cervix into the vagina in the subject the concentration of one or more inflammatory marker(s) selected from the group consisting of interleukin-6 (IL-6), IL-1β, IL-8, monocyte chemoattractant protein-1 (MCP-1), and GRO-α (Growth Related Oncogene-α); and
   2) predicting or diagnosing the risk for inflammation or infection in the subject if the concentration of IL-6 measured is higher than a cut-off value of 1 to 10 ng/ml, the concentration of IL-1β measured is higher than a cut-off value of 100 to 1000 pg/ml, the concentration of IL-8 measured is higher than a cut-off value of 1 to 30 ng/ml, the concentration of MCP-1 measured is higher than a cut-off value of 500 to 2500 pg/ml, or the concentration of GRO-α measured is higher than a cut-off value of 500 to 5000 pg/ml.

2. The method as set forth in claim 1, wherein the amniotic fluid leaked through the cervix into the vagina is collected with an amniotic fluid collecting apparatus.

3. The method as set forth in claim 2, wherein the amniotic fluid collecting apparatus is selected from the group consisting of a syringe, pipette, spoon, cotton swab, swab, Nelaton's catheter, and apparatus which can collect amniotic fluid leaked through the cervix into vagina.

4. A kit for prediction or diagnosis of inflammation or infection in amniotic fluid leaked through the cervix into the vagina, the kit comprising an antibody that specifically binds to a cytokine selected from the group of inflammatory markers consisting of IL-6, IL-1β, IL-8, MCP-1 and GRO-α, wherein a high risk of inflammation or infection is determined using the kit if the concentration of the cytokine bound to the antibody is as follows: the concentration of IL-6 is higher than a cut-off value of 1 to 10 ng/ml, the concentration of IL-1β is higher than a cut-off value of 100 to 1000 pg/ml, the concentration of IL-8 is higher than a cut-off value of 1 to 30 ng/ml, the concentration of MCP-1 is higher than a cut-off value of 500 to 2500 pg/ml, or the concentration of GRO-α is higher than a cut-off value of 500 to 5000 pg/ml.

5. The kit as set forth in claim 4, wherein the antibody is a monoclonal antibody or a polyclonal antibody.

6. The kit as set forth in claim 4, wherein the kit further comprises a detector that specifically binds to the antibody, a washing solution, and an enzyme reaction terminating solution.

7. The kit as set forth in claim 6, wherein the detector is a conjugate labeled with any one selected from the group consisting of chromogenic enzyme, a fluorescent material, a radioisotope, and a colloid.

8. The kit as set forth in claim 7, wherein if the conjugate is labeled with the chromogenic enzyme, the detector comprises a chromogenic substrate.

9. The kit as set forth in claim 4, wherein the amniotic fluid leaked through the cervix into the vagina is collected with a noninvasive amniotic fluid collecting apparatus.

10. A biochip for prediction or diagnosis of inflammation or infection in amniotic fluid leaked through the cervix into the vagina, the biochip comprising a solid substrate on which biomolecules are integrated, the biomolecules being selected from the group consisting of a low molecular weight compound, a ligand, an aptamer, a peptide, a polypeptide, a specific binding protein, a high molecular weight compound, and an antibody which binds specifically to a cytokine selected from the group of inflammatory markers consisting of IL-6, IL-β, IL-8, MCP-1, and GRO-α, wherein a high risk of inflammation or infection is determined using the biochip if the concentration of the cytokine bound to the biomolecules is as follows: the concentration of IL-6 is higher than a cut-off value of 1 to 10 ng/ml, the concentration of IL-1β is higher than a cut-off value of 100 to 1000 pg/ml, the concentration of IL-8 is higher than a cut-off value of 1 to 30 ng/ml, the concentration of MCP-1 is higher than a cut-off value of 500 to 2500 pg/ml, or the concentration of GRO-α is higher than a cut-off value of 500 to 5000 pg/ml.

11. The biochip as set forth in claim 10, wherein the solid substrate is selected from the group consisting of plastic, glass, metal, and silicon.

* * * * *